United States Patent [19]

Warriner

[11] Patent Number: Plant 5,647

[45] Date of Patent: Jan. 28, 1986

[54] ROSE PLANT JACFAR

[75] Inventor: William A. Warriner, Tustin, Calif.

[73] Assignee: Jackson & Perkins Company, Medford, Oreg.

[21] Appl. No.: 631,452

[22] Filed: Jul. 16, 1984

[51] Int. Cl.[4] ..... A01H 5/00

[52] U.S. Cl. ..... Plt./15

[58] Field of Search ..... Plt./15

*Primary Examiner*—Robert E. Bagwill

*Attorney, Agent, or Firm*—Manford R. Haxton

[57] ABSTRACT

A hybrid tea rose variety having a large plant producing long-stemmed blooms of a light yellow with no fragrance, approximately 27 petals, with numerous hooked prickles and numerous small prickles.

1 Drawing Figure

1

This present invention relates to a new and distinct variety of rose plant of the hybrid tea class which was originated by crossing the variety Redgold, U.S. Plant Pat. No. 3,006, with the variety Simplicity, U.S. Plant Pat. No. 4,089.

The primary objective of this breeding was to produce a new rose variety suitable for garden use, producing an abundance of blooms of a yellow hue on long stems of a vigorous, tall plant. This objective was substantially achieved along with other desirable improvements as evidenced by the following unique combination of characteristics which are outstanding in the new variety and which distinguish it from its parents as well as from all other varieties of which I am aware:

1. A hybrid tea plant producing long-stemmed flowers on a plant approximately 6 to 7 feet tall;
2. Buds of a light yellow color;
3. Large, open flowers with little fading from the bud color;
4. Little or no fragrance;
5. Approximately 27 petals plus a few large petaloids;
6. Large, hooked prickles and numerous small prickles.

Asexual reproduction of this new variety by budding, as performed at Wasco, Calif., shows that the foregoing characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color in terminology in accordance with The Royal Horticultural Society Colour Chart except where ordinary dictionary significance of color is indicated:

Parentage:
- *Seed parent.*—Redgold.
- *Pollen parent.*—Simplicity.

Classification:
- *Botanical.*—Rosa hybrid.
- *Commercial.*—Hybrid tea.

FLOWER

Observations made from specimens grown in a greenhouse at Irvine, Calif. in June.

2

Blooming habit: Continuous.

Bud:
- *Size.*—1¾" when petals start to unfurl.
- *Form.*—Long, pointed ovoid.
- *Color.*—When sepals first divide, near Yellow 12B; When half blown, upper side of petals near Yellow 12B; lower side of petals near Yellow 12B.
- *Sepals.*—Color: Green 138A. Three appendaged sepals lightly appendaged. Two appendaged sepals hairy edged with a few glands.
- *Receptacle.*—Color: Green 138A. Shape: Funnel. Size: Large, broad.
- *Peduncle.*—Length: Short. Surface: Prickly. Color: Light green. Strength: Stiff, erect.
- *Opening.*—Petals roll out gradually.

Open bloom:
- *Size.*—Large. Average open size 4½" to 5".
- *Borne.*—Singly, with occasional side buds.
- *Stems.*—Long, strong.
- *Form.*—When first open, high center. Permanence: Retains its form to the end, outer petal edges slightly curled.
- *Petalage.*—Number of petals under normal conditions: 27.
- *Color.*—Center of flower: Upper side of petals, near Yellow 6B; reverse side of petals, near Yellow 6B. Base of petals, Yellow 6C. Major color: Yellow 6B to 6D.
- *Variegations.*—None.
- *Discoloration.*—General tonality at end of third day: Yellow 6D.
- *Fragrance.*—None.

Petals:
- *Texture.*—Thick.
- *Shape.*—Round.
- *Form.*—Tips slightly recurved.
- *Arrangement.*—Loosely imbricated. Petaloids in center, few, large.
- *Persistence.*—Drop off cleanly.
- *Lastingness.*—On the plant, fair. As cut flower, fair.

Reproductive parts:
- *Anthers.*—Large. Color: Yellow. Arrangement: Regular around styles.
- *Filaments.*—Color: Yellow.
- *Pollen.*—Gold yellow.
- *Styles.*—Color: Greenish white.
- *Stigmas.*—Color: Greenish white.

PLANT

Form: Bush.

Growth: Very vigorous, upright. Reaches 6–7 feet tall under normal garden conditions at Irvine, Calif.

Foliage: Number of leaflets on normal mid-stem leaves: 5.

*Size.*—Large.

*Quantity.*—Normal.

*Color.*—New foliage: Greyed purple 183B. Old foliage: Normal green.

Leaflets:

*Shape.*—Oval.

*Texture.*—Leathery.

*Edge.*—Serrated.

*Serration.*—Single, small.

*Petiole.*—Rachis: Color: Green to reddish. Underside: With numerous prickles.

*Stipules.*—Very long, glandular edges.

*Disease resistance.*—Sightly susceptible to mildew under normal growing conditions at Irvine, Calif.

Wood:

*New wood.*—Color: Light green. Bark: Smooth.

*Old wood.*—Color: Green. Bark: Smooth.

Prickles:

*Quantity.*—On main canes from base: Ordinary. On laterals from main canes: Ordinary.

*Form.*—Long, hooked downward.

*Color when young.*—Green.

Small prickles:

*Quantity.*—On main stalks, many, on some stems. On laterals, many.

*Color.*—Green.

I claim:

1. A new and distinct variety of rose plant of the hybrid tea class, substantially as herein shown and described, characterized particularly as to novelty by the unique combination of large plant producing long-stemmed blooms of a light yellow with no fragrance, approximately 27 petals, with numerous hooked prickles and numerous small prickles.

* * * * *

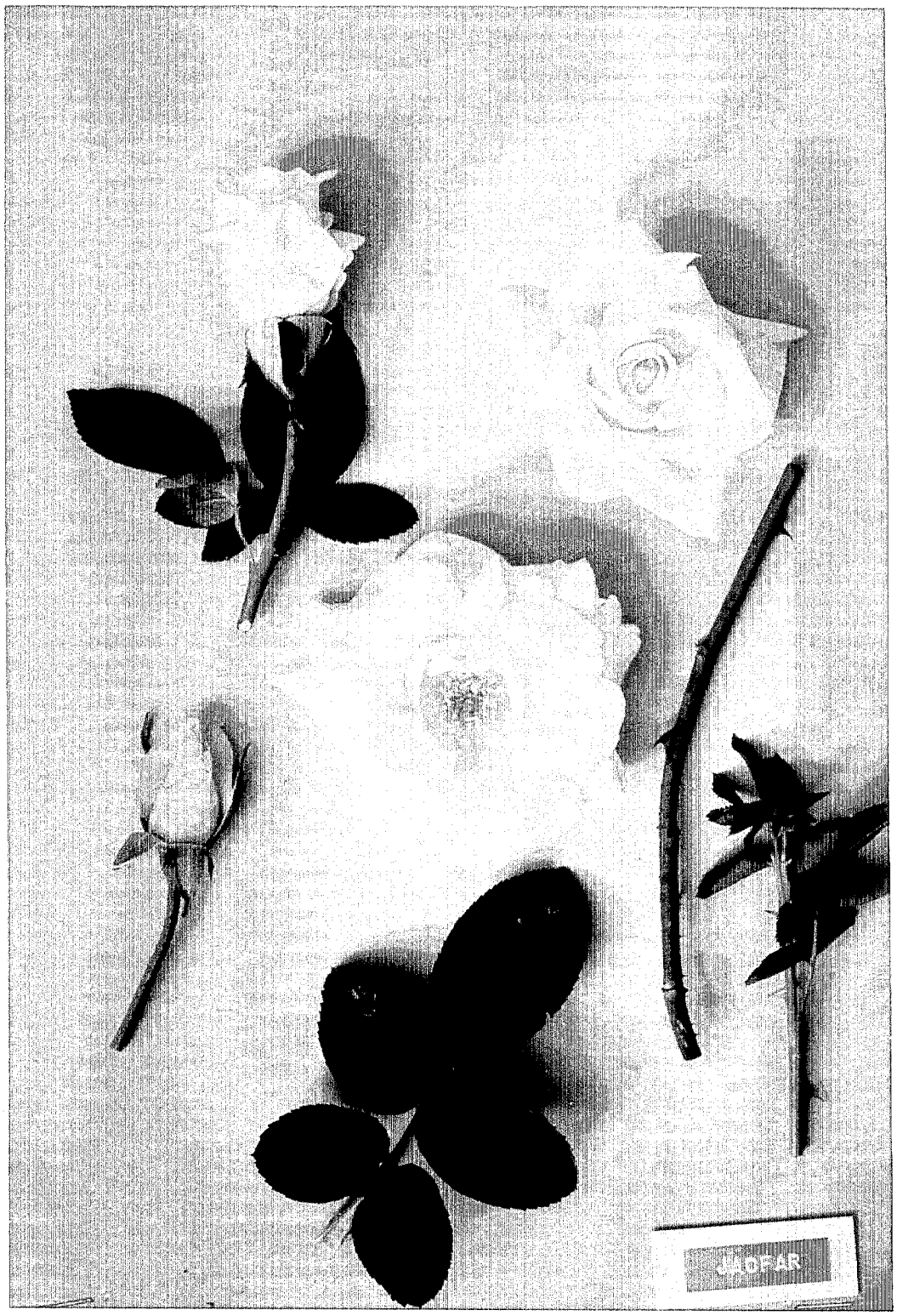
JAcOFAR